(12) United States Patent
Schöndube et al.

(10) Patent No.: US 11,845,044 B2
(45) Date of Patent: Dec. 19, 2023

(54) METHOD FOR PROCESSING A LIQUID SAMPLE

(71) Applicant: cytena Bioprocess Solutions co., Ltd., Taipei (TW)

(72) Inventors: Jonas Schöndube, Freiburg (DE); Cheng-Han Tsai, Freiburg (DE); Andre Gross, Freiburg (DE); Stefan Zimmermann, Bollschweil (DE); Peter Koltay, Freiburg (DE)

(73) Assignee: CYTENA BIOPROCESS SOLUTIONS CO., LTD., Taipei (TW)

( * ) Notice: Subject to any disclaimer, the term of this patent is extended or adjusted under 35 U.S.C. 154(b) by 1042 days.

(21) Appl. No.: 16/604,699

(22) PCT Filed: Apr. 13, 2018

(86) PCT No.: PCT/EP2018/059601
§ 371 (c)(1),
(2) Date: Oct. 11, 2019

(87) PCT Pub. No.: WO2018/189397
PCT Pub. Date: Oct. 18, 2018

(65) Prior Publication Data
US 2020/0123493 A1      Apr. 23, 2020

(30) Foreign Application Priority Data

Apr. 13, 2017    (LU) ........................................ 100170

(51) Int. Cl.
*B01F 3/04*       (2006.01)
*B01F 23/231*    (2022.01)
(Continued)

(52) U.S. Cl.
CPC ...... *B01F 23/23121* (2022.01); *B01F 31/651* (2022.01); *B01F 33/813* (2022.01); *C12M 23/12* (2013.01); *B01F 2101/23* (2022.01)

(58) Field of Classification Search
CPC .. B01F 23/23121; B01F 31/65; B01F 33/813; B01F 2101/23; B01F 31/651;
(Continued)

(56) References Cited

U.S. PATENT DOCUMENTS

| 2,956,931 A | 10/1960 | Goldberg |
| 5,839,828 A | 11/1998 | Glanville |

(Continued)

FOREIGN PATENT DOCUMENTS

| ES | 2898649 T3 * | 3/2022 |
| JP | S56-39776 A | 4/1981 |

(Continued)

OTHER PUBLICATIONS

Cytena Gmbh, "SCP Prototype User Manual," Version 2.7, Feb. 2016, Freiburg, Germany.

*Primary Examiner* — Charles S Bushey
(74) *Attorney, Agent, or Firm* — Hodgson Russ LLP

(57) ABSTRACT

The invention relates to a method for processing a liquid sample situated in a receptacle, wherein an attachment device is attached to the receptacle such that at least one fluid line protrudes into the liquid sample and a fluid is directly dispensed into the liquid sample through the fluid line and/or a portion of the liquid sample is aspirated into the fluid line.

14 Claims, 14 Drawing Sheets

Figure 1:
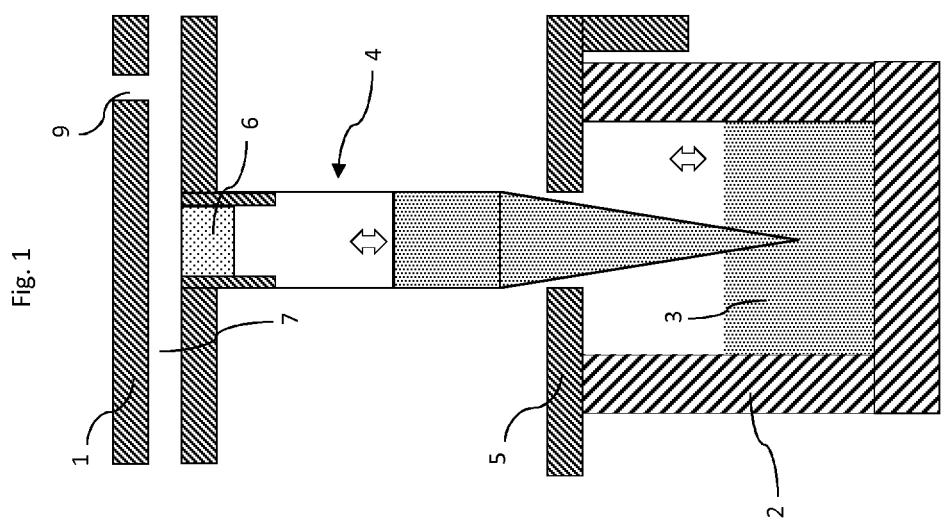

(51) Int. Cl.
*C12M 1/32* (2006.01)
*B01F 31/65* (2022.01)
*B01F 33/81* (2022.01)
*B01F 101/23* (2022.01)

(58) Field of Classification Search
CPC ..... B01J 19/0093; B01L 3/021; B01L 3/5027; C12M 23/12
See application file for complete search history.

(56) References Cited

U.S. PATENT DOCUMENTS

| | | | |
|---|---|---|---|
| 6,146,881 | A | 11/2000 | Hering |
| 6,869,571 | B2 * | 3/2005 | Ingenhoven ........... G01N 35/10 73/864.22 |
| 7,318,911 | B2 * | 1/2008 | Smith .................. B01L 3/0275 422/514 |
| 8,246,239 | B2 * | 8/2012 | Gorka ................. B01F 23/451 366/137 |
| 9,163,209 | B2 * | 10/2015 | Shioyama ............. C12M 45/02 |
| 2001/0028601 | A1 * | 10/2001 | Hiramatsu ............. B01F 31/65 366/167.1 |
| 2005/0180104 | A1 | 8/2005 | Olesen et al. |
| 2006/0177352 | A1 * | 8/2006 | Ziegmann ............. B01L 3/0275 422/400 |
| 2007/0099189 | A1 | 5/2007 | Gomez-Elvira Rodriguez et al. |
| 2007/0256510 | A1 | 11/2007 | Buchs et al. |
| 2009/0320622 | A1 | 12/2009 | Mueller et al. |
| 2010/0047898 | A1 * | 2/2010 | Bishop .................... B01F 31/65 264/171.12 |
| 2010/0124142 | A1 * | 5/2010 | Laugharn, Jr. ....... B01J 19/0046 366/108 |
| 2010/0206785 | A1 | 8/2010 | Beulay et al. |
| 2010/0278698 | A1 * | 11/2010 | Tajima ............... G01N 35/1065 422/522 |
| 2011/0189792 | A1 | 8/2011 | Reinhartz et al. |
| 2011/0296931 | A1 | 12/2011 | Warhurst |
| 2011/0318242 | A1 * | 12/2011 | Nay ..................... G01F 11/022 422/501 |
| 2012/0149603 | A1 | 6/2012 | Cooney et al. |
| 2014/0045253 | A1 * | 2/2014 | Zou ........................ C12M 23/42 435/317.1 |
| 2014/0106467 | A1 * | 4/2014 | Hutter ................ G01N 35/1016 436/180 |
| 2015/0259639 | A1 | 9/2015 | Silverman et al. |
| 2015/0299637 | A1 | 10/2015 | Park et al. |
| 2018/0008944 | A1 | 1/2018 | Ozeki |
| 2019/0255524 | A1 * | 8/2019 | Parry ..................... B01L 3/021 |

FOREIGN PATENT DOCUMENTS

| | | |
|---|---|---|
| JP | H05-30957 A | 2/1993 |
| JP | 2005140631 A | 6/2005 |
| JP | 2006-34235 A | 2/2006 |
| JP | 2006-167496 A | 6/2006 |
| WO | 02/072423 A1 | 9/2002 |
| WO | 2013/019212 A1 | 2/2013 |
| WO | 2014/091524 A1 | 6/2014 |

* cited by examiner

United States Patent 11,845,044 B2

METHOD FOR PROCESSING A LIQUID SAMPLE

CROSS-REFERENCE TO RELATED APPLICATIONS

The present application is the U.S. national phase of International Application No. PCT/EP2018/059601 filed Apr. 13, 2018, which claims priority of Luxembourgian Application No. 100170 filed Apr. 13, 2017, the entire disclosure of which is incorporated herein by reference.

FIELD OF THE INVENTION

The invention relates to a method for processing a liquid sample situated in a receptacle.

The invention further relates to an attachment device, and to a device comprising the attachment device according to the invention and a receptacle for the accommodation of the liquid sample.

BACKGROUND OF THE INVENTION

It is known from the prior art that active ingredients, such as, for example, monoclonal antibodies and other proteins, are produced with the aid of so-called monoclonal cell lines. These are populations of cells which all descend from an individual parent cell. It is necessary to produce monoclonal cell lines, since this is the only way to be able to ensure that all the cells in the population have an approximately identical genome for generating the active ingredients.

To generate a monoclonal cell line, cells are transferred individually into receptacles of a microtiter plate. The transferred cells are produced by genetically modifying a host cell line and individualizing these modified cells. The deposition of individual cells into the microtiter plates is done by, for example, open-jet printing methods or pipetting.

Afterwards, cell colonies growing from one cell are cultured statically, i.e., without movement, in the receptacles of the microtiter plate until they almost cover the entire base of the receptacles of the microtiter plate. Thereafter, the cell cultures are transferred in steps into larger vessels. In particular, the cell cultures are transferred into microtiter plates of different sizes and then into a shake flask and lastly into the bioreactor. Typically, a switch is made from static culture to dynamic culture in the case of shake flasks, i.e., the shake flasks are shaken continuously in order to mix the cell culture. Ultimately, from a series of many hundreds to thousands of such cell cultures, what is transferred into production is the one which can produce the active ingredients most stably and in the greatest quantity in a bioreactor.

In the bioreactor, the cell culture is typically kept in motion, and the pH, the oxygen and nutritional-value content and the temperature are adjusted to provide optimal growth conditions for the cells. Moreover, in a culture medium containing floating cells that is moved, it is possible to cultivate more cells per volume. In comparison with stationary cell cultures, this distinctly increases the production output while the volume remains the same.

Static culturing in microtiter plates is not ideal for the cells, since they are cultivated such that they behave ideally in a shaken or rocked environment. If the cells are transferred to static conditions, unwanted culture behavior may occur, such as, for example, reduction in metabolic activity and, in the worst case, the death of the cells. However, cells cannot be cultivated in bioreactors from the start, since the cell cultures do not grow at low concentrations. Thus, individual cells do not propagate in large volumes. The cell generally dies as a result. Therefore, it is necessary to increase in steps the volume in which the cell is situated.

The quantity of viable, propagating colonies and of the product obtained therefrom are essential to industry. They determine the turnover which can be generated with a production batch of cells.

What are known from the prior art are devices comprising shakers which shake the microtiter plates and thus the static conditions in the microtiter plate are prevented. However, a disadvantage of the known embodiments is that it is practically no longer possible to shake the microtiter plate in the case of receptacles having a small volume.

SUMMARY OF THE INVENTION

It is therefore an object of the invention to specify a method which can avoid the aforementioned disadvantages, irrespective of the volume of the receptacle.

The object of the invention is achieved by a method for processing a liquid sample situated in a receptacle, in which an attachment device is attached to the receptacle such that at least one fluid line protrudes into the liquid sample and a fluid is directly dispensed into the liquid sample through the fluid line and/or a portion of the liquid sample is aspirated into the fluid line.

It is a further object of the invention to specify a device which can avoid the aforementioned disadvantages, irrespective of the volume of the receptacle.

The object is achieved by an attachment device which carries out the method according to the invention. Furthermore, the object is achieved by an attachment device which is attachable in a detachable manner to a receptacle for the accommodation of a liquid sample, comprising at least one fluid line, the design and the intention of which are such that the fluid line protrudes into the liquid sample and that a fluid is directly dispensable into the liquid sample through the fluid line and/or a portion of the liquid sample is aspiratable into the fluid line.

The method according to the invention and the device have the advantage that the optimal production conditions for cell growth can already be realized very early in the production process. In particular, in the case of the method according to the invention and the device according to the invention, a movement and/or a mixing of the liquid sample can be realized and/or the gas content in the liquid sample and/or the nutrient content of the liquid sample and/or the cell concentration of the liquid sample can be adjusted. This is possible because the fluid line penetrates into the liquid sample and an aspiration of a portion of the liquid sample or a direct dispensing of a fluid into the liquid sample can be realized by means of the fluid line.

The liquid sample can be a liquid biological or chemical sample. In particular, the liquid sample can comprise cells floating in a liquid. The receptacle, which is not part of the attachment device, can be a microbioreactor. In a microbioreactor, certain chemical and/or biological reactions can proceed under defined conditions for the processing of the sample, with the reactions being inter alia controllable or regulatable by addition and/or removal of fluids. In particular, it is possible to culture cells, for example, in the microbioreactor.

The fluid line can be rigid. In particular, the fluid line can be a cannula. The fluid can be a gas or a liquid, especially the liquid sample, and is movable and can therefore be conducted and transported by means of pumps, valves, fluid lines, etc. The attachment device can thus dispense gas or liquid. A fluidic connection between two components exists when the fluid can flow from one component into the other component. Mixing of the liquid sample is understood to mean an operation in which the constituents of the liquid sample are moved relative to one another such that a new arrangement pattern arises.

In a particular embodiment, the dispensed fluid can be a previously aspirated portion of the liquid sample. Furthermore, as will be explained in detail below, the dispensed fluid can be a previously aspirated gas.

It is very particularly advantageous when the aspiration and dispensing is carried out multiple times in succession in order to mix the liquid sample and/or the aspiration and dispensing is carried out alternately in order to mix the liquid sample. The attachment device can comprise a control device or be connected to the control device. The control device can be designed to bring about an aspiration and dispensing multiple times in succession and alternately in order to mix the liquid sample. In particular, what can be brought about by the control device as a result of appropriate control of a pump is that the aspiration and dispensing is carried out multiple times in succession and/or alternately. Alternating aspiration and dispensing can be realized by reciprocal pumping. In particular, a pump element can be moved in a reciprocal manner for the mixing of the liquid sample. Alternatively or additionally, the control device can be designed such that what is brought about is that the dispensed fluid is the previously aspirated portion of the liquid sample or the previously aspirated gas.

The mixing of the liquid sample ensures that static conditions do not prevail in the receptacle. This means that ideal production conditions can be realized from the start, with the result that a rapid growth of, for example, cells can be realized. Furthermore, productivity is better predictable. Also, a better stability of the cell culture and a higher cell density are achieved than in the case of embodiments in which the cell cultures are cultured under static conditions.

In addition, the quantity of the aspirated liquid sample can be between 5% and 30% of the total quantity of the liquid sample. Also, the operation of aspiration and suction can be repeated at least 3 times, especially continuously for a predefined period of time. This can realize very particularly advantageous conditions for cell growth.

In a particular embodiment, the fluid dispensed into the liquid sample can be a gas. In this connection, the dispensed gas can be a gas previously aspirated from the liquid sample. The aspirated gas can be the gas which was chronologically previously dispensed into the liquid sample, especially from a gas tank or the environment, using the pump and by means of the fluid line. Alternatively, the aspirated gas can be gas from a gas bubble as described below.

In particular, the fluid can be oxygen or carbon dioxide. Oxygen is important for cell growth and carbon dioxide can be used for adjusting the pH. When gas is fed into the liquid sample, the gas bubbles can rise in the liquid sample. Gas can be fed after completion of the mixing of the liquid sample as a result of the operation of aspiration and dispensing of the liquid sample.

What is very particularly advantageous is an embodiment in which the gas bubble is generated, with a gas bubble diameter being increased and reduced in order to mix the liquid sample. In particular, the gas bubble can be generated at an outlet of the fluid line. An increase in the gas bubble diameter can be realized by dispensing of the previously aspirated gas from the fluid line. A reduction in the gas bubble diameter can be realized by aspiration of a portion of the gas from the gas bubble or of the entire gas from the gas bubble into the fluid line. The increase and reduction in the gas bubble diameter can be carried out multiple times in succession and/or alternately. This can improve the mixing of the liquid sample. In particular, the quantity of the aspirated gas can be between 50% and 100% of the total quantity of the gas bubble and/or the operation of aspiration and dispensing can be repeated at least 3 times, especially continuously for a predefined period of time.

As a result, the attachment device can realize a mixing of the liquid sample by, firstly, alternating dispensing of the liquid sample from the fluid line and aspiration of a portion of the liquid sample into the fluid line and by, secondly, increase and reduction in the gas bubble diameter. Both operations can be carried out simultaneously in one attachment device comprising multiple fluid lines. Alternatively, the operations can be carried out in a staggered manner.

The gas content in the liquid sample can be adjusted by feeding, especially controlled feeding, of the gas into the liquid sample. This can increase growth of the cell culture. The gas can be stored in a gas tank of the device that is fluidically connected to the fluid line. Furthermore, the device can comprise an adjustment device, such as, for example, a gas tank valve, by means of which the gas fed into the fluid line can be adjusted.

In this connection, in the case of a feeding, especially controlled feeding, of gas into the liquid sample, the gas content of the liquid sample can be adjusted by diffusion-based exchange between, firstly, the gas dispensed into the liquid sample and, secondly, the liquid sample. This embodiment is particularly advantageous when the receptacle has a small volume. In this connection, the gas can be fed into the liquid sample such that it rises in the liquid sample. Alternatively, the gas bubble can be generated at the outlet of the fluid line. The gas bubble can have a large diameter and thus a large contact surface. The large contact surface means that the diffusion-based exchange between the gas and the liquid sample can take place in a very particularly efficient manner.

Alternatively or additionally, the gas content can be adjusted by diffusion-based exchange between, firstly, the gas situated in the fluid line and, secondly, the liquid sample. In this embodiment, a gas rise is prevented by a particular design of the fluid line. To this end, multiple fingers, in particular exactly three, can extend from a wall of the fluid line in the longitudinal direction of the fluid line. The individual fingers can be arranged spaced apart in the circumferential direction of the fluid line.

Alternatively or additionally, the gas content of the liquid sample can be adjusted by diffusion-based exchange between, firstly, the gas situated in a section of the fluid line and, secondly, the liquid sample aspirated into the fluid line. In this embodiment, what is advantageous is a fluid-line design in which a wall of the fluid line has multiple projections, especially annular projections, which are arranged spaced apart in the longitudinal direction of the fluid line. The fingers can extend transversely, especially perpendicularly, in relation to the longitudinal direction of the fluid line.

In a very particular embodiment, what is carried out as desired by means of the attachment device is a mixing of the liquid sample or an aspiration of the liquid sample into the fluid line or a dispensing of fluid into the liquid sample. Thus, it is possible to carry out different processing steps using the attachment device.

After an interruption to the mixing of the liquid sample, a portion of the liquid sample can be aspirated into the fluid line after a predefined period of time has elapsed. This is especially advantageous when the sedimentation of solids in the liquid sample, such as, for example, biomass or cells, is to be waited for and thus only the supernatant is to be aspirated.

Alternatively, a portion of the liquid sample can be aspirated into the fluid line immediately after the interruption to the mixing. This is advantageous when a aliquot of the liquid sample is to be picked up.

After a portion of the liquid sample has been aspirated, the fluid line can be pulled out of the liquid sample and the attachment device, especially the fluid line, can be transported away from the receptacle. This can be done manually by the user or automatically by a transport device. The liquid sample is immobilized in the fluid line and cannot flow out of the fluid line by itself. Thus, the attachment device can be transported to a laboratory instrument, into which the liquid sample situated in the fluid line is dispensed.

Alternatively, the fluid line can be transported to another receptacle. The liquid sample situated in the fluid line can be dispensed into the other receptacle. If the other receptacle contains another liquid sample, the portion of the liquid sample that is situated in the fluid line can be dispensed into the other liquid sample.

In the case of provision of a sample carrier comprising multiple receptacles, the attachment device the fluid line can be moved into another position after the fluid line has been pulled out of one receptacle of the sample carrier, with the result that the fluid line penetrates into another receptacle of the sample carrier, where the liquid sample aspirated in the fluid line is dispensed. Naturally, it is also possible that, in the case of an attachment device comprising multiple fluid lines, what takes place is a parallel aspiration of the liquid samples or of the gas and/or a parallel dispensing of the liquid samples or of the gas. As a result, it is possible to carry out different work steps in different receptacles simultaneously by means of the attachment device.

Naturally, it is alternatively possible that a liquid from an external liquid tank not part of the device or of the attachment device is first aspirated into the fluid line of the attachment device. The attachment device is then transported to the receptacle and the liquid dispensed into the receptacle, especially for the first filling.

In a particular embodiment, the attachment device, especially the fluid line, can be fluidically connected to a pump. Furthermore, after the pump has been connected to the attachment device, the fluid line, especially all fluid lines, can be fluidically connected to the pump. Such an embodiment offers the advantage that a fluidic connection between the pump and the fluid line or the fluid lines can be realized in a simple manner, without further steps being necessary immediately after the connection of the pump to the attachment device.

In a very particular embodiment, when analyzing the liquid sample, a number, especially predefined number, of detection agents, especially microparticles and/or sensor spots, can be provided in the receptacle, the detection agents being intended for binding a chemical species of the liquid sample and for altering its optical properties, such as, for example, fluorescence, color and/or contrast, on the basis of the binding. Thereafter, the optical property of the detection agent can be ascertained.

Thereafter, the ascertained optical property of the detection agent can be used to determine the property of the liquid sample as the ascertained result and/or the ascertained optical property of the detection agent can be used to determine the presence and/or quantity of a species present in the liquid sample as the ascertained result.

The device can comprise an optical capture device, by means of which properties of the sample can be captured. Furthermore, the presence and/or the quantity of the species present in the liquid sample can be determined by means of the optical capture device. The optical capture device is connected to the control device of the device by means of data technology. The optical capture device can comprise an optical imaging device, especially a camera, by means of which an image of the liquid sample can be generated. This is possible because the receptacle is transparent in part.

The optical capture device can be arranged at an end of the receptacle that is facing away from the attachment. In the case of multiple receptacles, multiple optical capture devices can be provided, with each optical capture device being assigned to a single receptacle. Thus, images of each liquid sample can be generated.

The detected species can be chemical species in the liquid sample, such as, for example, dissolved gases, biomolecules, etc. A sensor spot can be a functionalized surface in the receptacle. The sensor spot can be arranged at a predefined section of the receptacle. The microparticles can be added to the liquid sample and/or be magnetic. The advantage thereof is that it is possible to avoid the microparticles also being aspirated when aspirating the liquid sample into the fluid line. Compared to sensor spots, microparticles offer the advantage that they can bind more molecules, since they can be moved through the entire liquid sample.

The liquid sample can be monitored taking into account the ascertained result. In particular, the culture conditions, such as, for example, the pH and/or the oxygen content, can be monitored. For instance, depending on the ascertained result, a warning signal can be outputted to the user and/or further processing steps can be initiated. Furthermore, the feeding of fluid into the liquid sample or a removal of fluid from the liquid sample can be regulated taking into account the ascertained result. For example, it is possible on the basis of the ascertained result to determine that the receptacle has insufficient liquid. Therefore, new liquid can be introduced into the receptacle by means of the attachment device. Alternatively, it is possible to establish by means of the ascertained result that the gas content of the liquid sample is too low, with the result that gas is fed into the liquid sample by means of the attachment device. Furthermore, the ascertained result can be used to select the most promising cell culture. In this connection, the more promising a cell culture, the higher the number of biomolecules produced.

In a particular embodiment, a filter which is liquid-impermeable and gas-permeable can be arranged in the fluid line. The liquid sample being able to flow into the attachment is avoided by the provision of the filter.

In addition, the fluid line can be implemented with the attachment in an integral manner or in a detachable manner. Furthermore, the fluid line can be fluidically connected to the attachment. The attachment can cover the receptacle and/or support itself on the receptacle. Furthermore, the attachment can be connected to the receptacle in a detachable manner.

Furthermore, the embodiment can comprise a lid which is arrangeable on and/or attachable to the receptacle, especially directly. In particular, the lid can rest on the receptacle. The lid can have a through-hole, through which the fluid line extends.

The fluid line can be pipette-shaped. Alternatively, the fluid line can have a constant cross section toward the receptacle, especially toward a receptacle base. Furthermore, the fluid line can have a tapering cross section, especially continuously tapering cross section, toward the receptacle, especially toward a receptacle base. Also, the outer surface of the fluid line can rest on an inner wall of the receptacle. The shape of the fluid line, especially the diameter of the fluid line, can be chosen such that the flow velocity and the quantity of the aspirated liquid sample are sufficiently high so that a mixing of the sample can be realized. Furthermore, the fluid line can be implemented such that an external side of the fluid line is hydrophobic. This can prevent liquid residues from adhering to the fluid line in a simple manner.

The attachment or the lid can close off the receptacle in a sealing manner. In particular, the attachment or the lid can comprise a seal, such as, for example, an O-ring. Thus, the evaporation of the liquid sample from the receptacle can be prevented.

In a very particular embodiment, the attachment device can comprise at least one valve, by means of which the fluid line is closable. Thus, what can be controlled by means of the valve is whether the fluid, especially gas, is fed to the fluid line. The valve can be connected to the control device and the valve position can be controlled by the control device. In the case of provision of multiple fluid lines, each fluid line can be assigned to a valve. The valves can each be connected to the control device, with the result that the control device can control the valve position of the various valves.

In a very particular embodiment, the attachment device can comprise at least one further fluid line which protrudes into the liquid sample and through which a further fluid is dispensed into the sample. This means that the further fluid line penetrates into the same receptacle as the fluid line. The further fluid can be identical to the fluid. Alternatively, the dispensed fluid can correspond to the portion of the previously aspirated liquid sample and the further fluid can be the gas. In this embodiment, a portion of the liquid sample can be aspirated or the aspirated portion can be dispensed by means of the fluid line, and gas can be dispensed into the receptacle by means of the further fluid line.

The attachment device can comprise at least one other fluid line which protrudes into another liquid sample of another receptacle, the fluid line and the other fluid line being fluidically connected and the liquid sample and the other liquid sample being aspirated into the fluid line and into the other fluid line, respectively, such that the liquid sample is not mixed with the other liquid sample. To this end, it is possible to envisage the control device controlling, for example, the pump such that there is no mixing of the liquid sample with the other sample. Thus, an undesired mixing of the liquid sample with the other liquid sample can be avoided in a particularly simple manner. The liquid sample and the other liquid sample can be identical. Alternatively, the liquid sample and the other liquid sample can differ from one another.

What is particularly advantageous is a device in which the attachment device is attached with the receptacle. The attachment device, especially the fluid line or the fluid lines, can be fluidically connected to the pump. In this connection, the pump can be implemented such that the aspiration of the fluid and the dispensing of the fluid can be realized by reciprocal movement of a pump element. The pump can be implemented as a pneumatic pump or a peristaltic pump or a piezo micropump.

The device can also comprise multiple pumps. This is especially advantageous in the case of an attachment device which comprises multiple fluid lines and in which the fluid lines are not fluidically connected to one another. For instance, it is possible for at least one fluid line to be fluidically connected to one pump and at least one other fluid line to be fluidically connected to another pump.

The fluid line can be fluidically connected to the pump by means of a fluid channel. If the pump is not directly fluidically connected to the fluid channel, but by means of a hose to the pump, the fluid channel can be connected to the pump by means of the hose. The other fluid line can be fluidically connected to the other pump by means of another fluid channel. If the other pump is not directly fluidically connected to the fluid channel, but by means of another hose to the pump, the other fluid channel can be connected to the other pump by means of the other hose. In addition, the fluid channel and/or the other fluid channel can be arranged in the attachment. The fluid channel can be fluidically connected to multiple fluid lines and/or the other fluid channel can be fluidically connected to multiple other fluid lines. As a result, a simply constructed attachment device is provided.

In a very particular embodiment, a sample carrier can comprise multiple receptacles. The receptacle can have a volume of 100 µl. The sample carrier can be a microtiter plate. The microtiter plate can be a plate having 6 or 24 or 96 or 384 or 3456. Naturally, the microtiter plate can also comprise more receptacles. In addition, the microtiter plate can be a rectangular plate and/or consist of plastic. The receptacles, which are isolated from one another, can be arranged in rows and columns. The individual receptacles can contain different liquid samples.

The sample carrier is implemented such that the receptacles are not fluidically connected to one another when the attachment device is removed. In particular, there are no fluid lines in walls of the sample carrier, via which at least two receptacles are fluidically connected to another.

The attachment device can comprise multiple fluid lines which extend from the attachment in the same direction. In particular, each fluid line can be identical to the above-described fluid line. Furthermore, each of the fluid lines can penetrate into a receptacle of the sample carrier. In addition, it is naturally possible for multiple fluid lines to penetrate into the same receptacle.

The fluid channel, especially the fluid channels, in the attachment can be designed and implemented such that only gas flows in the and/or through the fluid channel. This means that the fluid channel, especially the fluid channels, are implemented such that no liquid flows through the fluid channel. Thus, a flow of liquid between two receptacles can be avoided in a simple manner. In particular, the fluid channel, especially the fluid channels, can be designed and implemented such that, under the same pump performance in the conveyance of gas or liquid, only the gas can flow through the fluid channel, especially the fluid channels.

This can be achieved by the fluid channel, especially the fluid channels, being designed such that they have a fluidic resistance that is high to the extent that only gas can flow through the fluid channel, especially the fluid channels. A high fluidic resistance can, for example, be achieved by an appropriate design of the fluid channel, especially the fluid channels. Furthermore, the fluid surface of the fluid channel, especially the fluid channels, that comes into contact with the fluid can be designed such that it counteracts wetting, and this is likewise a resistance to a flow of liquid and ultimately prevents this.

The attachment device can be implemented such that the processing steps carried out by means of the individual fluid lines differ from one another. For instance, it is possible by means of a fluid line of the attachment device that penetrates into a receptacle to dispense a gas into the liquid sample. In the case of a first other fluid line which penetrates into a first other receptacle, a portion of the other liquid sample can be aspirated into the other fluid line and/or dispensed. Also, it is possible by means of a second other fluid line that penetrates into a second other receptacle to realize a mixing of the further liquid sample by alternating aspiration and dispensing, especially of gas or fluid. This is possible because the attachment device can comprise at least one valve, especially multiple valves, with the control device being able to control the valve position and/or the individual fluid lines being fluidically connected to different fluid channels. The different fluid channels can be fluidically connected to different pumps. Naturally, it is possible for multiple fluid lines to penetrate into the receptacle, the first other receptacle and/or second other receptacle.

BRIEF DESCRIPTION OF THE DRAWING VIEWS

Figure 2:
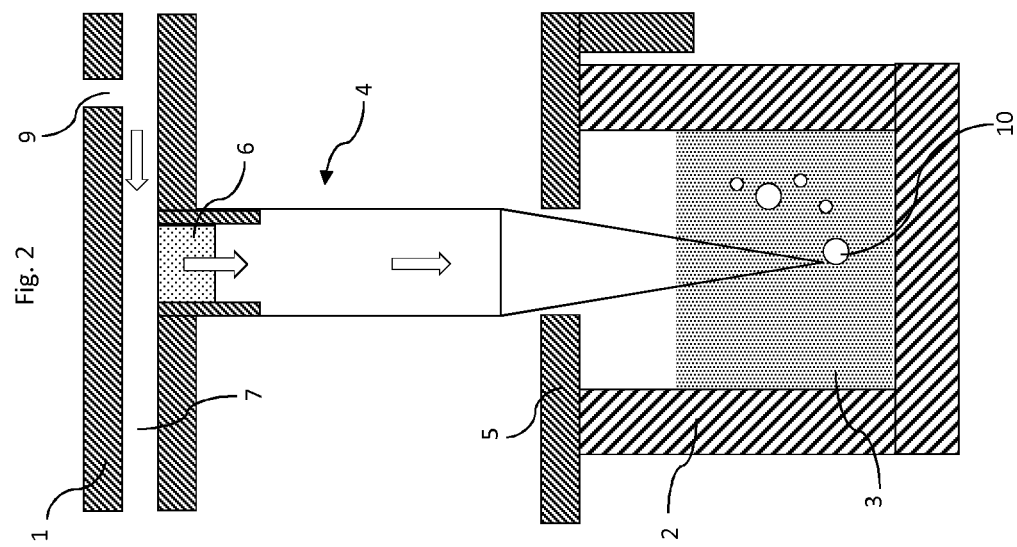
Figure 3:
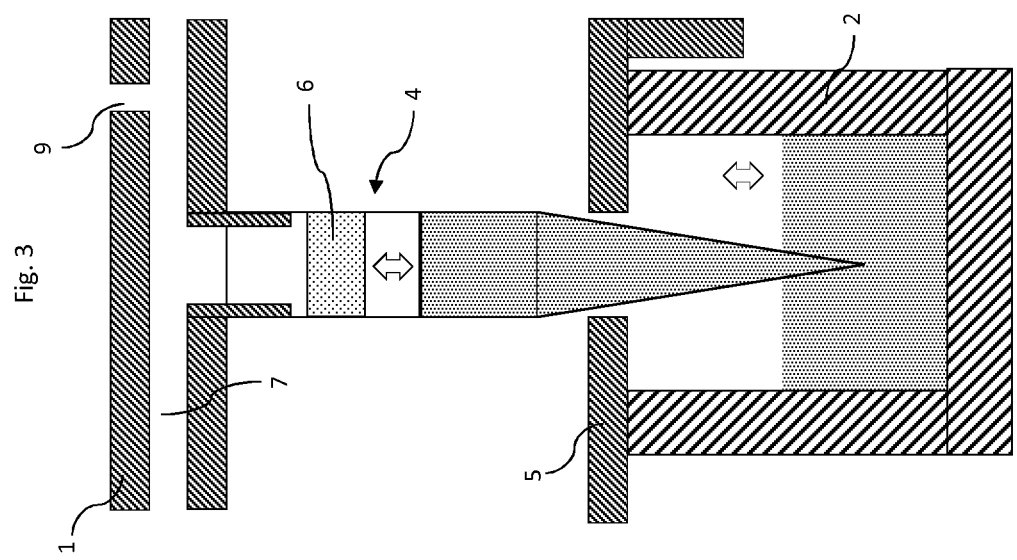
Figure 4:
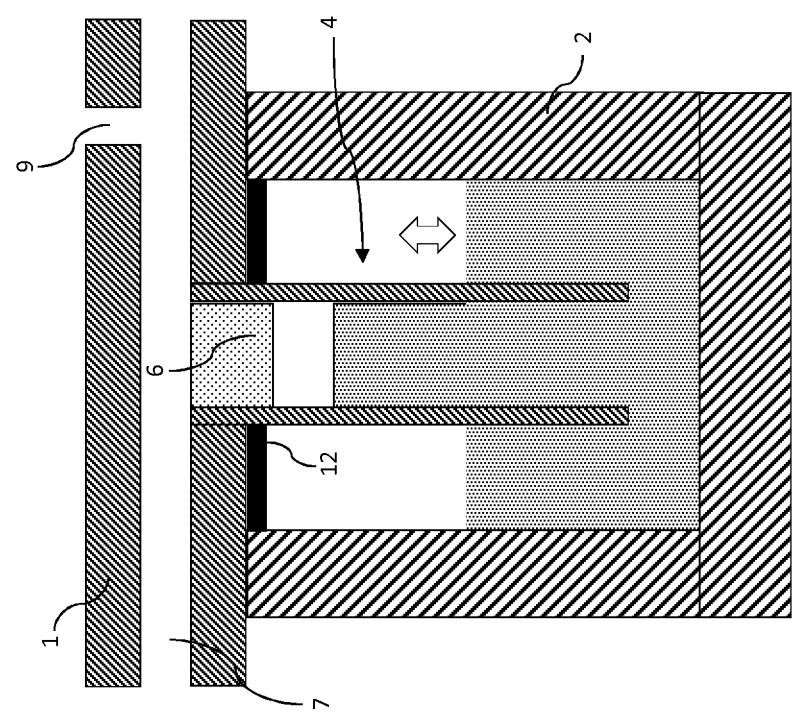
Figure 5:
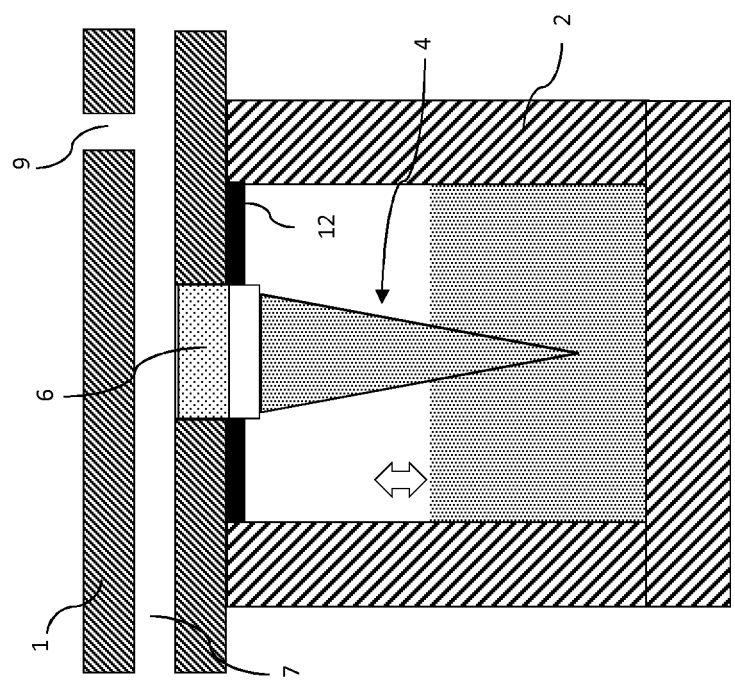
Figure 6:
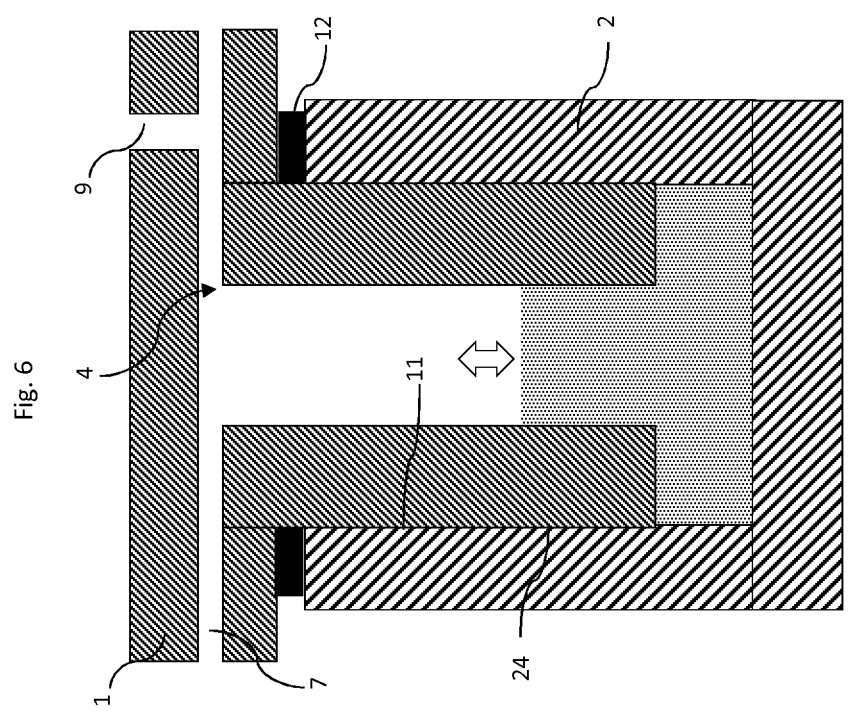
Figure 7:
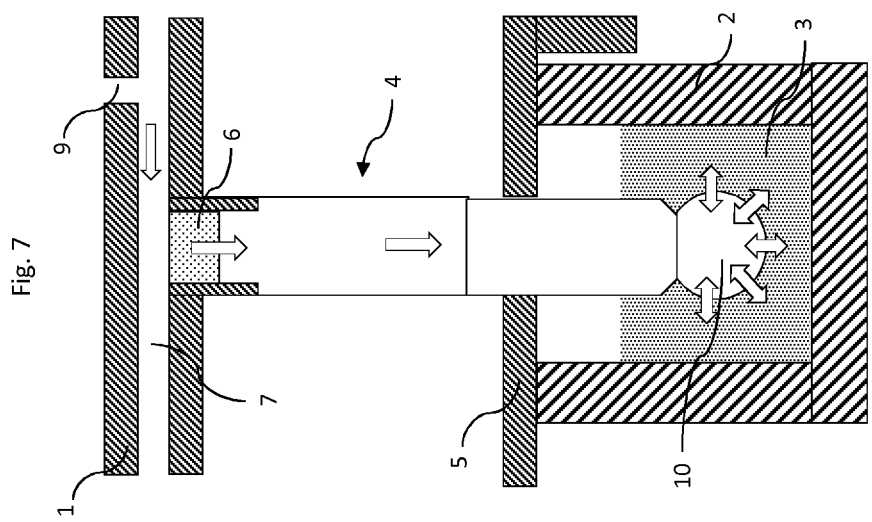
Figure 8:
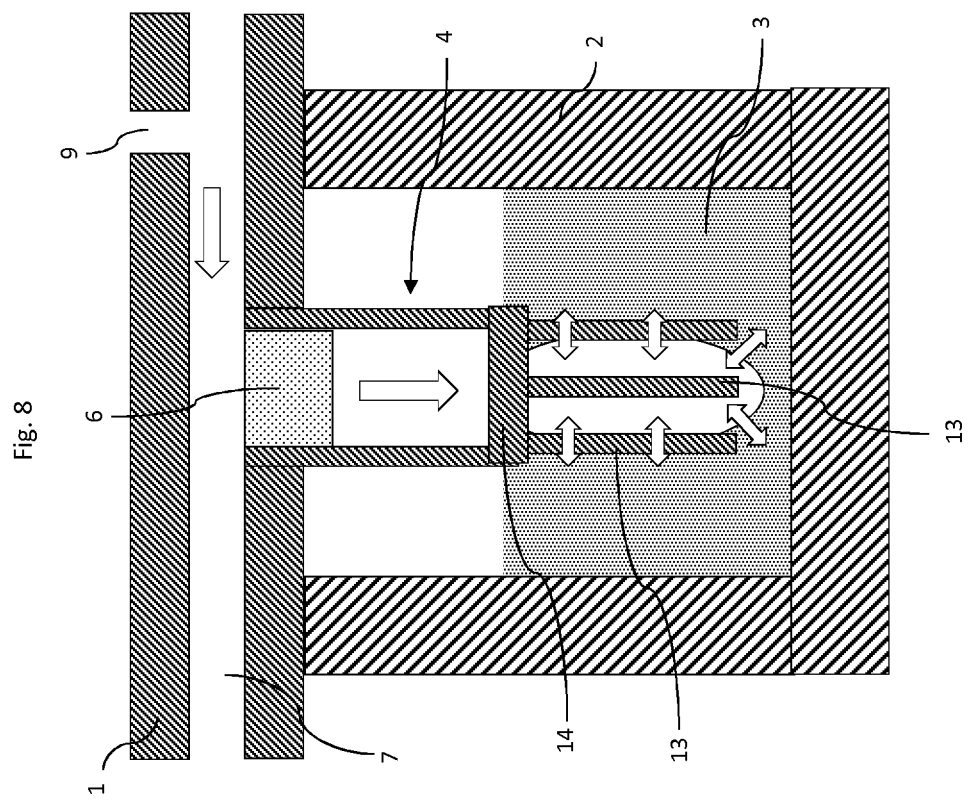
Figure 9:
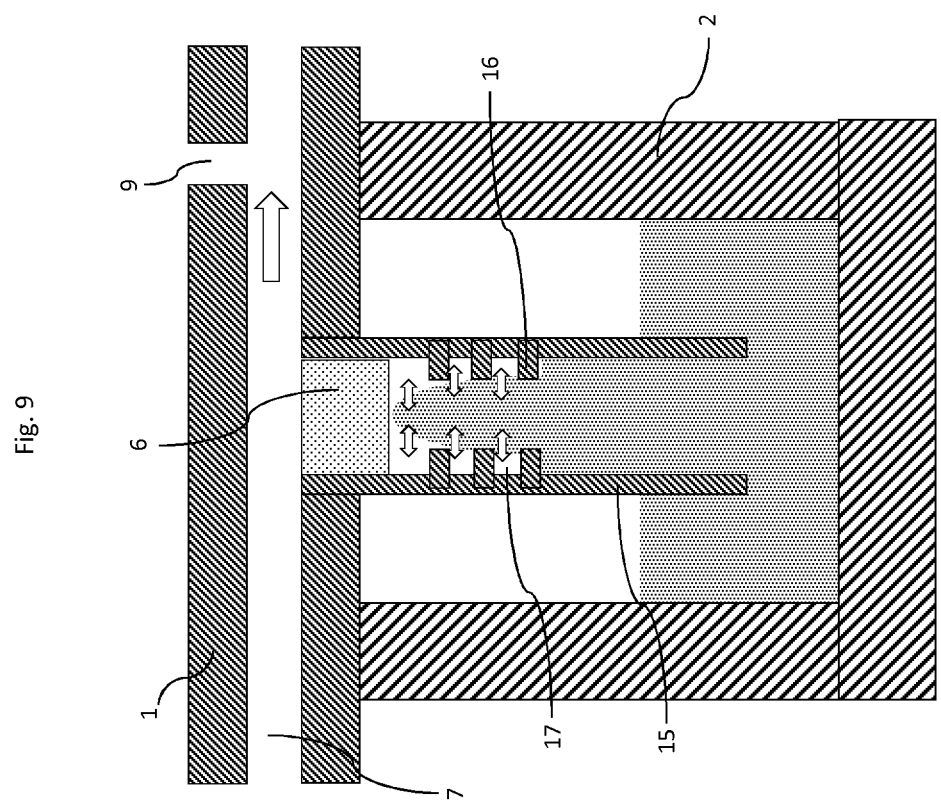
Figure 10:
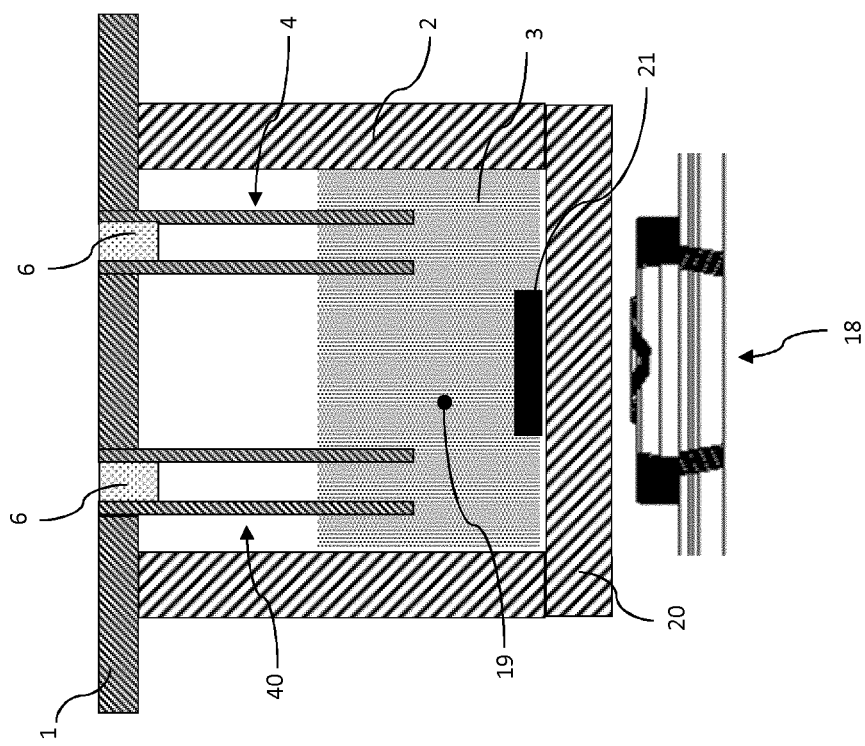
Figure 11:
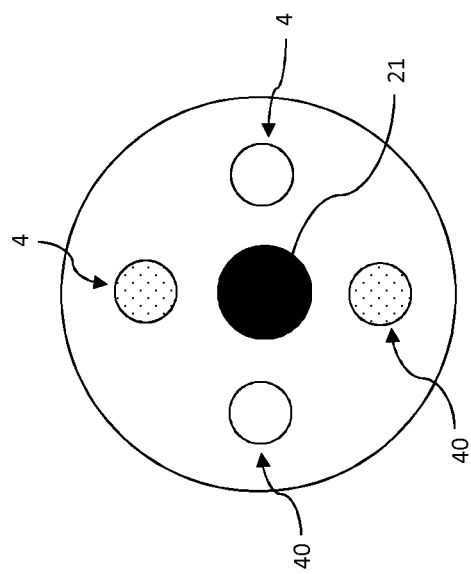
Figure 12:
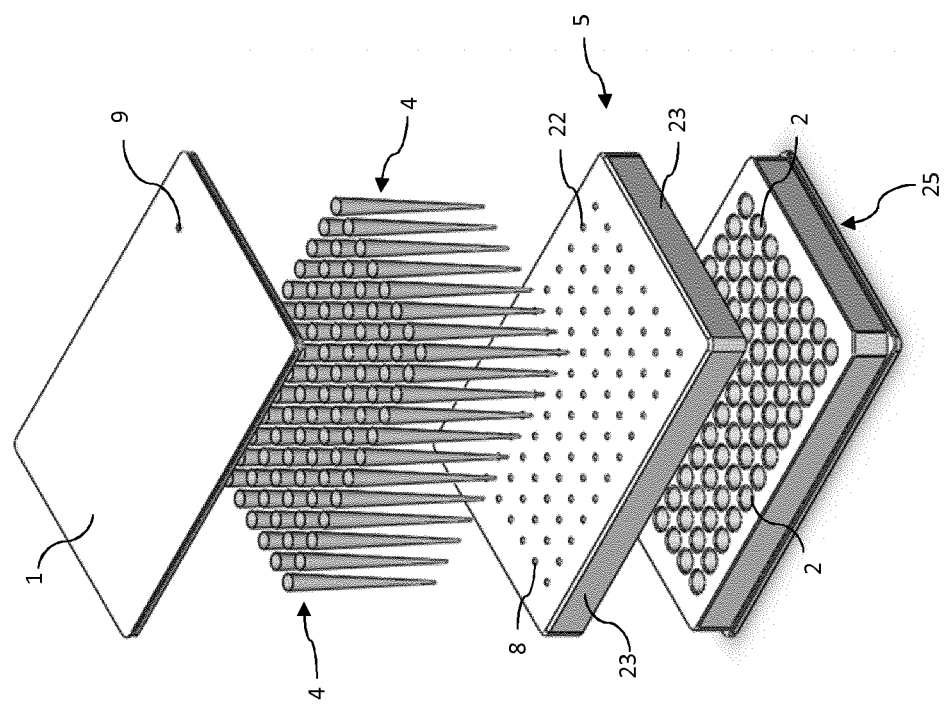
Figure 13:
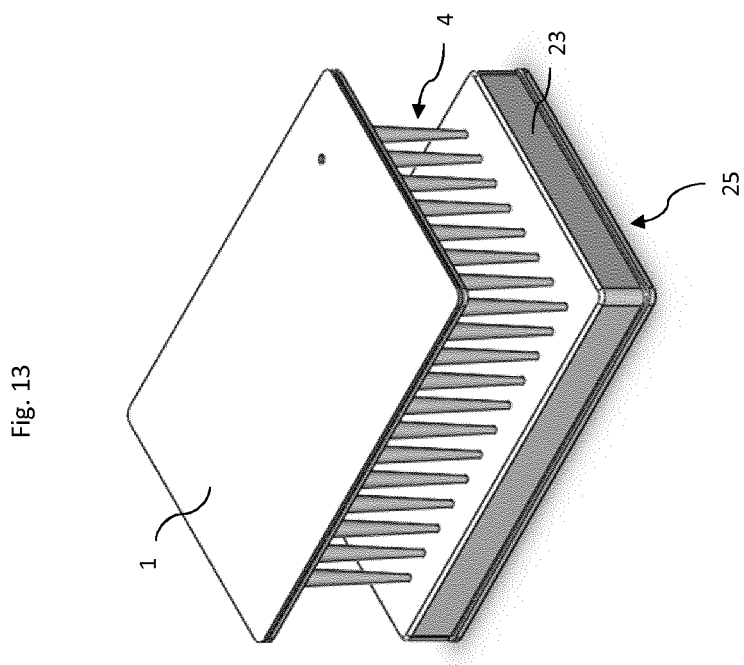
Figure 14:
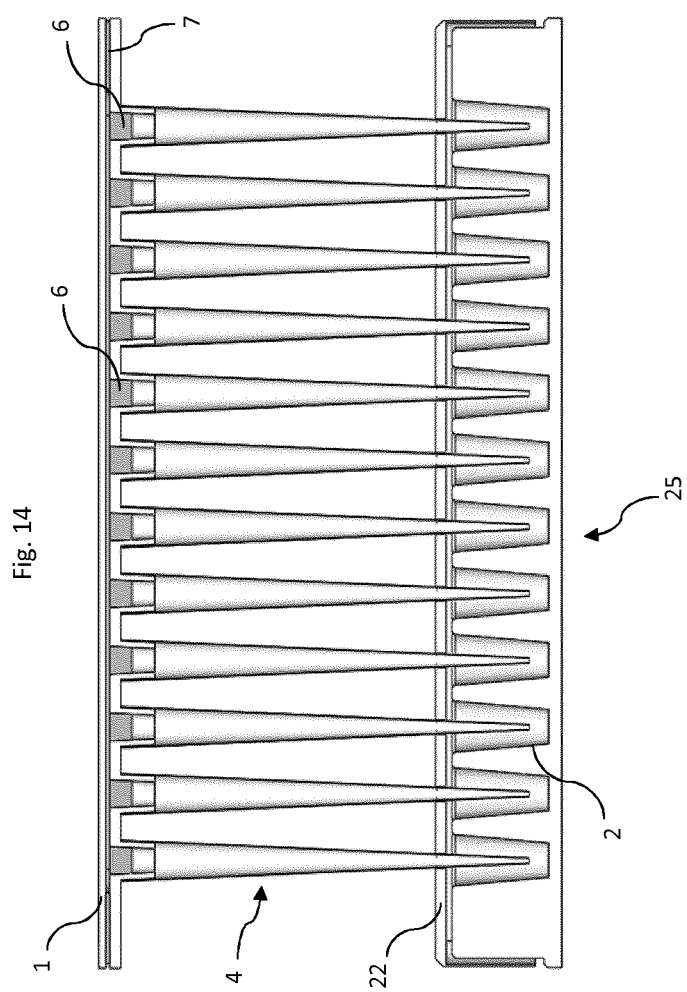

The subject matter of the invention is schematically represented in the figures, with the same components or components having the same effect mostly being provided with the same reference signs. In the figures:

FIG. 1 shows a schematic representation of a device comprising an attachment device according to a first exemplary embodiment and a receptacle, FIG. 2 shows a schematic representation of the device comprising the attachment device according to the first exemplary embodiment and a receptacle, with gas being fed by means of a fluid line, FIG. 3 shows a schematic representation of a device comprising an attachment device according to a second exemplary embodiment and a receptacle, FIG. 4 shows a schematic representation of a device comprising an attachment device according to a third exemplary embodiment and a receptacle, FIG. 5 shows a schematic representation of a device comprising an attachment device according to a fourth exemplary embodiment and a receptacle, FIG. 6 shows a schematic representation of a device comprising an attachment device according to a fifth exemplary embodiment and a receptacle, FIG. 7 shows a schematic representation of a device comprising an attachment device according to a sixth exemplary embodiment and a receptacle, FIG. 8 shows a schematic representation of a device comprising an attachment device according to a seventh exemplary embodiment and a receptacle, FIG. 9 shows a schematic representation of a device comprising an attachment device according to an eighth exemplary embodiment and a receptacle, FIG. 10 shows a schematic representation of a device comprising an attachment device according to a ninth exemplary embodiment and a receptacle, FIG. 11 shows a top view of the device depicted in FIG. 10, FIG. 12 shows an exploded view of a device comprising an attachment device according to a tenth exemplary embodiment and a microtiter plate, FIG. 13 shows a perspective view of the device comprising the attachment device and the microtiter plate as shown in FIG. 12 in the assembled state, and FIG. 14 shows a lateral sectional view of the device comprising the attachment device and the microtiter plate as shown in FIG. 12.

DETAILED DESCRIPTION OF THE INVENTION

The device shown in FIG. 1 comprises an attachment device according to a first exemplary embodiment and a receptacle 2, with the receptacle 2 accommodating a liquid sample 3. The attachment device is attached to the receptacle 2 in a detachable manner. In addition, the attachment device comprises a fluid line 4 which is designed and intended to protrude into the liquid sample 3.

A fluid, especially a previously aspirated portion of the liquid sample, can be directly dispensed into the liquid sample 3 through the fluid line 4 and/or a portion of the liquid sample 3 can be aspirated into the fluid line 4. The aspiration and dispensing can be carried out alternately and/or multiple times in succession. Thus, the level of the liquid sample 3 within the fluid line 4 and the receptacle 2 can vary, and this is symbolized in FIG. 1 by the double arrow in both cases. As a result of the operation of aspiration and dispensing, mixing of the liquid sample 3 situated in the receptacle 2 is achieved.

The attachment device comprises an attachment 1, which is fluidically connected to the fluid line 4, and a lid 5, which covers the receptacle 2 and is directly connected to the receptacle 2. The lid 5 has a through-hole 8, through which the fluid line 4 extends in order to plunge into the liquid sample 3. The fluid line 4 supports itself, especially in the vertical direction, on the lid 5, and so the attachment 1 is indirectly mounted on the receptacle 2 via the fluid line 4. The fluid line 4 is connected to the attachment 1 in a detachable manner.

A filter 6 is arranged within the fluid line 4. The filter 6 is liquid-impermeable and gas-permeable. This means that the portion of the liquid sample 3 that has been aspirated into the fluid line 4 cannot flow through the filter 6. However, a gas can flow through the filter 6. The filter 6 is arranged in an end of the fluid line 4 that is distant from the liquid sample 3.

The attachment 1 comprises a fluid channel 7, which is fluidically connected to the fluid line 4, especially to a channel situated in the fluid line 4. Also, the fluid channel 7 is fluidically connected to an opening 9 in the attachment 1. The attachment 1 is fluidically connected to a pump, which is not depicted, by means of the opening 9. By means of the pump, it is possible to vary the pressure in the fluid channel 7 and thus the fluid line 4 in order to bring about an aspiration of a portion of the liquid sample 3 into the fluid line 4 or a dispensing of the aspirated portion of the liquid sample 3 into the receptacle.

The attachment device depicted in FIG. 2 differs from the attachment device described in FIG. 1 only in its mode of operation. Thus, in the attachment device depicted in FIG. 2, gas is fed into the liquid sample 3 by means of the fluid line 4. Along the direction of the single arrows which have been drawn in, the gas flows via the opening 9 into the fluid channel 7 and, from there, into the fluid line 4 and the liquid sample 3. In this process, the gas flows through the filter 6. In this mode of operation, there is thus no repeated and/or alternate aspiration and dispensing in order to mix the liquid sample 3. Specifically, the goal of this mode of operation is to adjust the gas content of the liquid sample 3.

The exemplary embodiments described below can be operated with the two above-described modes of operation in analogy to the exemplary embodiment depicted in FIGS. 1 and 2.

FIG. 3 shows a schematic representation of the attachment device according to a second exemplary embodiment. The attachment device differs from the exemplary embodiment depicted in FIGS. 1 and 2 in the arrangement of the filter 6. Thus, in the second exemplary embodiment, the filter 6 is no longer arranged at the end of the fluid line 4 that is distant from the liquid sample 3, but in an intermediate region of the fluid line 4.

FIG. 4 shows a schematic representation of the attachment device according to a third exemplary embodiment. The attachment device differs from the exemplary embodiment depicted in FIGS. 1 and 2 in that the attachment device does not comprise lid 5. Thus, the attachment 1 is directly placed onto the receptacle 2 and connected thereto in a detachable manner. Furthermore, the attachment 1 comprises a seal 12, by means of which the receptacle 2 is sealed.

A further difference is the design of the fluid line 4. Whereas the fluid line 4 depicted in FIGS. 1 and 2 is pipette-shaped with a tip that tapers toward the liquid sample 3, the fluid line 4 depicted in FIG. 4 has a constant cross section.

FIG. 5 shows a schematic representation of the attachment device according to a fourth exemplary embodiment. This differs from the exemplary embodiment depicted in FIG. 4 in the design of the fluid line 4. Thus, the fluid line 4 has a continuously tapering cross section toward the liquid sample 3.

FIG. 6 shows a schematic representation of the attachment device according to a fifth exemplary embodiment. This differs from the third exemplary embodiment depicted in FIG. 4 in the design of the fluid line 4. Thus, the fluid line 4 is implemented such that its external side 11, especially an external side of the wall of the fluid line 4, is directly in contact with an internal side 24 of the receptacle 2. In addition, the fluid line 4 has a relatively large diameter, and so a larger quantity of liquid sample 3 can be aspirated into the fluid line 4 than in the fluid line 4 depicted in FIG. 4. The cross section of the fluid line 4 is constant.

FIG. 7 shows a schematic representation of the attachment device according to a sixth exemplary embodiment. The attachment device differs from the exemplary embodiment depicted in FIG. 2 in the design of the fluid line 4 and in the manner of how the gas is fed to the liquid sample 3.

One difference is that the fluid line 4 has a virtually constant cross section. In particular, the fluid line 4 depicted in FIG. 7 has, at its outlet, a larger diameter than the fluid line 4 depicted in FIG. 2. Furthermore, in the exemplary embodiment depicted in FIG. 7, a gas bubble 10 is generated at the outlet of the fluid line 4. To this end, gas is, along the direction of the single arrows which have been drawn in, fed via the opening 9, the fluid channel 7 and the fluid line 4 toward the outlet of the fluid line 4. In addition, a diffusion-based exchange between the gas bubble 10 and the liquid sample 3 can occur, as symbolized by the double arrow. Thus, in contrast to the embodiment depicted in FIG. 2, the dispensed gas is held at the outlet of the fluid line 4 and it is prevented from rising in the liquid sample 3.

In an alternative mode of operation, the attachment device can be operated such that the diameter of the gas bubble 10 is increased or reduced. Reduction is achieved by aspirating at least a portion of the gas of the gas bubble 10 into the fluid line 4. In this mode of operation, it is possible to realize mixing of the liquid sample 3 by alteration of the gas bubble diameter.

The attachment device according to a seventh exemplary embodiment as depicted in FIG. 8 differs from the embodiment depicted in FIG. 4 in that there is no seal. A further difference is the design of the fluid line 4.

The fluid line 4 comprises multiple fingers 13 which extend from an intermediate piece 14 of the fluid line 4 in the longitudinal direction of the fluid line 4. In addition, the fingers 13 are arranged adjacent to one another and/or spaced apart in the circumferential direction of the fluid line 4. This means that, when seen in the circumferential direction, there is a gap between every two fingers 13. The fingers 13 prevent the gas fed into the fluid line 4 from rising in the liquid sample 3. Thus, a diffusion-based exchange can occur between, firstly, the gas immobilized by the fingers 13 and, secondly, the liquid sample 3, especially across the gap between the fingers 13, as symbolized by the double arrows. Proceeding from the opening 9, the gas is fed toward the liquid sample 3 in the direction of the single arrows which have been drawn in.

The attachment device depicted in FIG. 9 differs from the attachment device depicted in FIG. 8 in the design of the fluid line 4. Thus, the fluid line 4 does not comprise any fingers 13, but instead comprises multiple annular projections 16 which protrude from a wall 15 of the fluid line 4 in a perpendicular manner in relation to the longitudinal axis of the fluid line 4. Furthermore, the projections 16 are arranged adjacent to one another and/or spaced apart in the longitudinal direction of the fluid line 4.

When a portion of the liquid sample 3 is aspirated, the liquid sample 3 penetrates into the fluid line 4. At the same time, what is formed between every two projections 16 adjacent in the longitudinal direction of the fluid line 4 is a gas space 17, into which the liquid sample 3 does not penetrate. Thus, a diffusion-based exchange can occur between, firstly, the liquid sample 3 penetrated into the fluid line 4 and, secondly, the gas situated in the gas space 17, as symbolized by the double arrow. The portion of the liquid sample 3 is aspirated by suction of the gas situated in the fluid line 4 and/or the fluid channel 7 across the opening 9 in the direction of the single arrow.

FIG. 10 shows a schematic representation of the attachment device according to a ninth exemplary embodiment. FIG. 11 shows a top view of the attachment device.

The attachment device comprises multiple fluid lines 4, especially exactly two, and multiple further fluid lines 40, especially exactly two. Both the fluid lines 4 and the further fluid lines 40 protrude into the liquid sample. In one mode of operation of the attachment device, gas can be fed to the liquid sample through the two further fluid lines 40. In the remaining two fluid lines 4, what can take place in both cases is an alternating aspiration of a portion of the liquid sample and a dispensing of the previously aspirated portion of the liquid sample in order to mix the liquid sample 3.

Although not depicted in the figures, the four fluid lines are fluidically connected to the same fluid channel 7 situated in the attachment 1. In particular, FIG. 10 does not depict the part of the attachment 1 that faces away from the receptacle 2 and that forms the upper limit of the fluid channel 7. Naturally, other modes of operation are also possible, in which gas is fed to the liquid sample 3 via fewer than or more than two further fluid lines 40 and/or a mixing of the liquid sample 3 by means of aspiration and dispensing can be realized through more than or fewer than two fluid lines 4.

Alternatively, a mixing of the liquid 3 sample can be realized by the two further fluid lines 40, by increasing and reducing the gas bubble diameter. By means of the fluid lines 4, a mixing of the liquid sample 3 by aspiration of a portion of the liquid sample 3 and dispensing of the aspirated portion of the liquid sample 3 can be realized at the same time or in a staggered manner.

In addition to the attachment device and the receptacle 2, the device also comprises an optical capture device 18 for the capture of a property of the liquid sample 3. The optical capture device 18 is arranged at an end of the receptacle 2 that is facing way from the attachment 1 and can comprise an optical imaging device, such as a camera. By means of the optical imaging device, it is possible to generate an image of the liquid sample 3.

Microparticles 19 are arranged within the liquid sample 3. Furthermore, a sensor spot 21 is situated on a receptacle base 20. By means of the images generated by the optical imaging device, the optical capture device 18 can inter alia capture the presence of a chemical species and/or some physical properties of the liquid sample. This result can be transferred to a control device, which is not depicted.

FIG. 12 shows an exploded view of a device comprising an attachment device according to a tenth exemplary embodiment and a microtiter plate 25. The attachment device differs from the previous attachment devices in that a multiplicity of fluid lines 4 extend from the attachment 1 toward the microplate 25. The attachment 1 and/or the fluid lines 4 can be designed as in any embodiment disclosed in FIGS. 1 to 11. Furthermore, the embodiment depicted in FIG. 12 can be operated in analogy to the embodiments described in FIGS. 1 to 11.

The lid 5 is box-shaped and comprises a top side 22, which is placed onto the microtiter plate 25, and edge sections 23, which extend from the top side 22 toward the microtiter plate 25. Also, the lid 5 comprises a multiplicity of through-holes 8. In particular, the number of through-holes 8 corresponds to the number of receptacles 3 in the microtiter plate 25 and to the number of fluid lines 4. The microtiter plate 25 comprises a multiplicity of receptacles 2, in which liquid samples not depicted in the figure, such as, for example, cell cultures, are situated. The individual receptacles 2 are not fluidically connected to one another.

As is evident from FIG. 13, which shows the device in an assembled state, the lid 5 covers all the receptacles 3 of the microtiter plate 25. In particular, the lid 5 is implemented such that it is directly placed onto the microtiter plate 25. As a result, when the samples present in the receptacles 3 are mixed, the lid 5 can prevent said samples from flowing out of the receptacles 3.

Each of the fluid lines 4 extends through a through-hole 8 in order to penetrate into the receptacle 3. The attachment 1 is arranged above the lid 5 and comprises an opening 9. The attachment 1 can be fluidically connected to a pump, which is not depicted, by means of the opening 9.

As is evident from FIG. 14, the opening 9 is fluidically connected to the fluid channel 7 situated in the attachment 1. The fluid channel 7 extends through the attachment 1. Each of the fluid lines 4 is fluidically connected to the fluid channel 7. Naturally, embodiments in which not all fluid lines are fluidically connected to the fluid channel 7, but to another, nondepicted fluid channel, are also conceivable. In addition, the other fluid channel is not fluidically connected to the fluid channel 7. In this case, the attachment 1 additionally comprises a further, nondepicted opening, which is fluidically connected to another, nondepicted pump. The attachment device comprises a multiplicity of valves, which are not depicted in the figures. The valve position of the individual valves can be controlled by the nondepicted control device of the device. By means of the control device, it is possible to control the valves in a specific manner in order to realize a flow of fluid toward certain fluid lines 4 and thus toward certain receptacles 2.

The fluid lines 4 each extend directly from the attachment 1 and are connected thereto in a detachable manner. In this connection, the fluid lines 4 are intended for and appropriately designed for immersion in each case into a liquid sample 3 situated in the receptacle. The liquid sample is not depicted in FIG. 14.

LIST OF REFERENCE SIGNS

1 Attachment
2 Receptacle
3 Liquid sample
4 Fluid line
5 Lid
6 Filter
7 Fluid channel
8 Through-hole
9 Opening
10 Gas bubble
11 External side
12 Seal
13 Finger
14 Intermediate piece
15 Wall
16 Projections
17 Gas space
18 Optical capture device
19 Microparticle
20 Receptacle base
21 Sensor spot
22 Top side
23 Edge sections
24 Internal side
25 Microtiter plate
40 Further fluid line

What is claimed is:

1. A method for processing a liquid sample (3) situated in a receptacle (2), wherein an attachment device is attached to the receptacle (2) such that at least one fluid line (4) of the attachment device is fluidically connected to an opening (9) of the attachment device by way of a fluid channel (7) of the attachment device extending transversely relative to a direction of the at least one fluid line (4), and the at least one fluid line (4) protrudes into the liquid sample (3) and a fluid is directly dispensed into the liquid sample (3) through the fluid line (4) by applying a positive pressure to the fluid line (4) through the fluid channel (7) and a portion of the liquid sample (3) is aspirated into the fluid line (4) by applying a negative pressure to the fluid line (4) through the fluid channel (7), wherein the dispensed fluid is a gas previously aspirated from the liquid sample (3), wherein a gas bubble (10) is generated on the end of the fluid line (4) within the liquid sample (3) in the receptacle (2), wherein a diameter of the gas bubble (10) is pneumatically increased and reduced to mix the liquid sample (3) within the receptacle (2).

2. The method as claimed in claim 1, wherein
   a. the aspiration and dispensing is carried out multiple times in succession in order to mix the liquid sample (3) and/or
   b. the aspiration and dispensing is carried out alternately in order to mix the liquid sample (3).

3. The method as claimed in claim 1, wherein the quantity of the aspirated liquid sample (3) is between 5% and 30% of the total quantity of the liquid sample (3) and the operation of aspiration and dispensing is repeated at least 3 times.

4. The method as claimed in claim 1, wherein
   a. a gas content of the liquid sample (3) is adjusted by feeding of the gas into the liquid sample (3) and/or
   b. a gas content of the liquid sample (3) is adjusted by diffusion-based exchange between the liquid sample (3) and the gas and/or between, firstly, the gas situated in the fluid line and, secondly, the liquid sample (3) and/or c. a gas content of the liquid sample (3) is adjusted by diffusion-based exchange between, firstly, the gas situated in a section of the fluid line (4) and, secondly, the portion of the liquid sample (3) aspirated into the fluid line (4).

5. The method as claimed in claim 1, wherein a mixing of the liquid sample (3) or an aspiration of the liquid sample (3) into the fluid line (4) or a dispensing of fluid from the fluid line (4) into the liquid sample (3) is achieved.

6. The method as claimed in claim 5, wherein the mixing of the liquid sample (3) is interrupted and
   a. the portion of the liquid sample (3) is aspirated into the fluid line (4) after a predefined period of time has elapsed or
   b. the portion of the liquid sample (3) is aspirated into the fluid line (4) immediately after the interruption to the mixing.

7. The method as claimed in claim 1, wherein, after the portion of the liquid sample (3) has been aspirated, the fluid line (4) is pulled out of the liquid sample (3) and transported away from the receptacle (2).

8. The method as claimed in claim 7, wherein the fluid line (4) is transported to a further receptacle (2) and the liquid sample (3) situated in the fluid line (4) is dispensed into the further receptacle.

9. The method as claimed in claim 5, wherein the fluid line (4) is fluidically connected to a pump.

10. The method as claimed in claim 9, wherein the mixing of the liquid sample (3) is realized by reciprocal pumping.

11. The method as claimed in claim 1, wherein the liquid sample (3) is analyzed to provide an ascertained result, wherein when the liquid sample (3) is analyzed,
   a. a number of detection agents are provided in the receptacle (2) and/or in the liquid sample (3), the detection agents being intended for binding a chemical species of the liquid sample (3) and for altering optical properties of the liquid sample on the basis of the binding, and
   b. an optical property of the liquid sample (3) resulting from provision of the detection agents is ascertained and
   c. the ascertained optical property is used to determine a property of the liquid sample (3) as the ascertained result and/or the ascertained optical property is used to determine the presence and/or quantity of a species present in the liquid sample (3) as the ascertained result.

12. The method as claimed in claim 11, wherein a feeding of fluid into the liquid sample (3) or removal of fluid from the liquid sample (3) is regulated taking into account the ascertained result.

13. The method as claimed in claim 1, wherein the attachment device comprises a further fluid line (40) which protrudes into the liquid sample (3) and through which a further fluid is dispensed into the liquid sample (3).

14. (previously presented; withdrawn) The method as claimed in claim 1, wherein the attachment device comprises another fluid line which protrudes into another liquid sample of another receptacle, the fluid line (4) and the other fluid line being fluidically connected, a portion of the liquid sample (3) and a portion of the other liquid sample being aspirated into the fluid line (4) and into the other fluid line, respectively, such that the aspirated liquid sample (3) is not mixed with the aspirated other liquid sample.

* * * * *